(12) United States Patent
Müller et al.

(10) Patent No.: US 6,783,949 B1
(45) Date of Patent: Aug. 31, 2004

(54) PROCESSES FOR DETERMINING WHETHER A TEST SUBSTANCE CONTAINS LIPASES OR LIPASE INHIBITORS

(75) Inventors: Günther Müller, Sulzbach (DE); Stefan Petry, Frankfurt (DE); Holger Jordan, Weilrod (DE); Horst Kleine, Hattersheim (DE); Horst Wenzel, Frankfurt (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/562,022

(22) Filed: May 1, 2000

(30) Foreign Application Priority Data

Apr. 30, 1999 (DE) .......................................... 199 19 634

(51) Int. Cl.$^7$ ................................................ C12Q 1/44
(52) U.S. Cl. ........................... 435/19; 435/18; 435/69.2
(58) Field of Search ............................... 435/19, 4, 18, 435/69.2, 198, 94.6; 424/450, 502

(56) References Cited

U.S. PATENT DOCUMENTS 4,668,623 A * 5/1987 Kinnunen et al. ............. 435/19

FOREIGN PATENT DOCUMENTS

EP 0 253 271 A1 1/1988

OTHER PUBLICATIONS

Monti J. Real Time Fluorescence Polarization Measurements. J of Biochem and Biophys Methods. 11(1)45–57, 1985.*
Muller G. Analysis of Lipid Metabolism in Adipocytes Using a Fluorescent Fatty Acid Derivative. Biochimica et Biophysica Acta 1347(1)23–39, 1997.*
Ting et al. (1990). Detection of a phosphatidylinositol–specific phospholipase C at the surface of Swiss 3T3 cells and its potential role in the regulation of cell growth. The Journal of Biological Chemistry 265(10): 5337–5340.*
Johnson et al. (1980). Dansyl Phosphatidylethanolamine–labeled Very Low Density Lipoproteins. The Journal of Biological Chemistry 255(8): 3451–3465.*
R. Schmid et al., "Lipases: Interfacial Enzymes with Attractive Applications," *Angew. Chem. Int. Ed.*, 37:1608–1633 (1998).
H. S. Hendrickson, "Fluorescence–Based Assays of Lipases, Phospholipases, and other Lipolytic Enzymes," *Anal. Biochem.*, 219:1–8 (1994).
R. Schmid et al., "Lipasen: Grenzflächen–Enzyme mit attraktiven Anwendungen," *Angew. Chem.*, 110:1694–1720 (1998), no English Language Translation Provided.
P. Strålfors et al., "Phosphorylation of Hormone–sensitive Lipase by Cyclic AMP–dependent Protein Kinase," *J. Biol. Chem.*, 258(24):15146–15152 (1983).
B. Bhattacharyya et al., "Maytansine Binding to the Vinblastine Sites of Tubulin," *FEBS Lett.*, 75(1):159–165 (1977).
D. Sklan et al., "Association of Acylglyceride and Retinyl Palmitate Hydrolase Activities with Zinc and Copper Metalloproteins in a High Molecular Weight Lipid–Protein Aggregate Fraction from Chick Liver Cytosol," *Biochimica et Biophysica Acta*, 711:532–538 (1982).
G. Müller et al., "Analysis of lipid metabolism in adipocytes using a fluorescent fatty acid derivative. I. Insulin stimulation of lipogenesis," *Biochimica et Biophysica Acta*, 1347:23–39 (1997).
A. Ting et al., "An improved synthesis of 7–nitrobenz–2–oxa–1,3–diazole analogs of CDP–diacylglycerol and phosphatidylinositol," *Chem. Phys. Lipids*, 60:83–91 (1991).

* cited by examiner

*Primary Examiner*—Ralph Gitomer
(74) *Attorney, Agent, or Firm*—Finnegan, Henderson, Farabow, Garrett & Dunner, L.L.P.

(57) ABSTRACT

Processes for determining whether a test substance contains lipases or lipase inhibitors are provided. Processes for determining the activity of lipases or lipase inhibitors are also provided. Furthermore, processes for the preparation of micelle or vesicle substrates comprising monoacylglyceride having a fluorescent label are described.

9 Claims, No Drawings

PROCESSES FOR DETERMINING WHETHER A TEST SUBSTANCE CONTAINS LIPASES OR LIPASE INHIBITORS

This applications claims benefit to German Patent Application No. 199 19 634.6 filed Apr. 30, 1999.

The invention relates to a simple continuous test for the identification of structures which favor the arrangement of aromatics to give charge-transfer complexes, such as, for example, complex phospholipid/lipid structures (bilayer, monolayer, aggregates, micelles), with the aid of synthetic fluorescence-labeled acylglycerides, and its use for determination of the activity of lipases/lipase inhibitors.

Lipases, phospholipases, and other lipolytic enzymes have great importance in the biotechnological and medical field. In certain metabolic disorders, increased lipase activity in the fatty tissue can be detected, which is held partly responsible for the pathogenesis of this disease. The greatest part of the energy reserves of the body is stored in cells of the fatty tissue as fatty acids of the triglycerides. The essential anabolic processes caused by insulin include the stimulation of the uptake of substrates for triglyceride synthesis and the increase in lipogenesis. A further important process caused by insulin is the inhibition of lipolysis, the process by means of which catabolic hormones, primarily catecholamines, stimulates the hydrolysis of triglycerides and thereby induce the release of fatty acids. An important problem which is linked with noninsulin-dependent diabetes mellitus (NIDDM) has its cause in the uninhibited lipolysis of the fat cells, which leads to increased levels of unesterified fatty acids in the plasma. According to a present idea, the fatty acids stimulate gluconeogenesis in the liver and decrease the glucose utilization in the skeletal muscle by means of still poorly characterized molecular mechanisms. In fact, it was possible to show that the suppression of lipolysis in fat cells by inhibitors of lipolysis, such as agonists of the nicotinic acid receptor of the fat cell, lowers both the fatty acid concentrations in the plasma and raised blood sugar in diabetic animals and patients. Unfortunately, these beneficial effects are not particularly strongly pronounced and only of relatively short duration. This may be based on a physiological counterregulation caused by intervention in the regulatory mechanism of the rate-determining enzyme of lipolysis, the hormone-sensitive lipase (HSL). There are good reasons to assume that the inhibition of the lipolytic reaction will lead to an improved therapy of NIDDM, at least with respect to the suppression of the fatty acid release from the fat cells. The direct inhibition of HSL by suitable inhibitors should in this case get around the obvious difficulties of an intervention into the complex regulation of HSL.

The activity of lipolytic enzymes is traditionally investigated using radiometric, titrimetric, enzymatic, or fluorimetric/photometric methods. Radiometric assays are the most sensitive, but they require expensive radiolabeled substrates, are discontinuous, and require the separation of the radiolabeled substrate from the radiolabeled product. Such separations are often troublesome and the avoidance/reduction of radioactive waste is of increasing importance (especially relevant if there are a large number of tests).

Titrimetric tests are continuous and can be carried out both with natural and synthetic substrates, but they frequently suffer from a fairly low sensitivity and are susceptible to conditions that influence the amount of protons released.

Enzymatic or chromatographic methods for the detection of one of the products of the lipolytic reaction (e.g., glycerol) are very sensitive and relatively robust, but are also complicated in terms of handling, as they demand the working-up of the incubation batch of the lipase reaction before the actual enzymatic/chromatographic detection. The coupling of an enzyme test allows only endpoint measurements ("time-stop" measurement). Furthermore, in the investigation of unknown substances (e.g., searching for potential inhibitors), an effect on the enzymes of the detection reaction cannot be excluded in principle and therefore necessitates appropriate controls.

These considerations gave the impetus to the development of fluorimetric/photometric processes. In principle, these achieve the sensitivity of radiometric methods but necessitate the use of synthetic substrates or samples modified with fluorophores or chromophores. Traditional fluorimetric/photometric methods, like the radiometric procedures, are discontinuous in course and necessitate the separation of the substrate from the product. Recently, continuous fluorimetric/photometric assays have been developed (S. Hendrickson, *Analyt. Biochem* 219 (1994) 1–8), which are based on a shift in the fluorescence or extinction maximum of the product in comparison with the substrate. However, all these processes are restricted to the detection of phospholipases, lipoprotein lipase (LPL), cholesterol esterase, sphingomyelinase, and glucosylceramide glucosidase. Substrates having fluorophoric/chromophoric groups, suitable for the continuous activity measurement of tryglyceride-cleaving enzymes (e.g., HSL, monoglyceride lipase, diglyceride lipase, triglyceride lipase, LPL, pancreatic lipase, hepatic lipase, bacterial lipase, phospholipase $A_2$ ($PLA_2$), phospholipase C (PLC), cholesterol esterase), are as yet unknown.

It is therefore the aim of the invention to develop a simple continuous test for the identification of structures which favor the arrangement of aromatics to give charge-transfer complexes, such as complex phospholipid/lipid structures (bilayer, monolayer, aggregates, micelles), with the aid of synthetic fluorescence-labeled acylglycerides, and a process for determination of the activity of lipid-binding proteins, such as lipases.

Lipid transporters are proteins that recognize lipids and do not cleave like lipases, but instead transport through biological membranes.

Lipases are understood here as meaning biologically relevant endogenous lipases, such as are defined, for example, in R. D. Schmid, R. Verger, *Angew. Chem.* 110 (1998) 1694–1720.

A hormone-sensitive enzyme is understood as meaning an enzyme that is influenced in its activity by secondary messengers (e.g., cyclic adenosine monophosphate (cAMP)) of dependent phosphorylation or by means of other allosteric mechanisms (e.g., protein-protein interaction) which are under hormone control. Hormones that regulate the CAMP level are, for example, adrenalin, noradrenalin, glucagon, and insulin.

The invention relates to a process for the preparation of a substrate, comprising a) reacting a fatty acid provided with a fluorescent label with 2,3-epoxypropanol to give a monoacylglyceride in alcoholic solution, such as, for example, $C_1$–$C_4$-alkanol, preferably methanol, at room temperature with addition of a base, such as, for example, a non nucleophilic inorganic base, preferably alkali metal carbonates and alkali metal $C_1$–$C_4$-alkanolates, particularly preferably methanolates, such as sodium methanolate or potassium methanolate, b) subjecting this monoacylglyceride to ultrasonic treatment with phospholipids in the ratio (mg/ml) 1:10 to 10:1, preferably 1:2 to 3:1, and particularly preferably 1:1 to 1.5:1, from which the substrate results, which is recognizable by a color change from yellow to red.

A fluorescent label is defined as a chemical group within a molecule, which, after excitation by light, is itself capable of emitting light. Such groups are employed here in order to prepare substances which themselves are still detectable in lowest concentrations of about 1 nM. Mention may be made, for example, of N,N-dimethylaminosulfonic acid (dansyl) or 4-chloro-7-nitrobenzo-2-oxa-1,3-diazole (NBD), preferably NBD.

A fatty acid is understood, for example, as meaning a long-chain carboxylic acid, which is saturated or unsaturated and has a chain length of C-8 to C-20, preferably C-12, C-14, C-16, and C-18 which is saturated or unsaturated, particularly preferably C-12 and saturated.

A fatty acid provided with a fluorescent label was coupled to a monoacylglyceride using 2,3-epoxypropanol. From this synthetic substrate and phospholipids, such as, for example, phosphatidylinositol and phosphatidylcholine on their own or together, optionally in a ratio by weight of 10:1 to 1:10, preferably 3:1 to 1:3, particularly preferably 2:1, micelles or vesicles which serve as a substrate of the lipase to be investigated were formed by ultrasonic treatment which lasts, for example, for about 1 to 10 minutes, preferably 1 to 6 minutes, particularly preferably 4 minutes. This incorporation into micelles or vesicles is associated with a color change from yellow to red, based on a charge-transfer complex of the aromatics, which are spatially closely adjacent in this structure. Incubation with lipase leads to the removal of the fatty acids with release of labeled fatty acid and glycerol.

As phospholipids, for example, phosphatidylcholine (6 mg) and phosphatidylinositol (6 mg) are dissolved in chloroform (1 ml each). For the preparation of the substrate, two parts of phosphatidylinositol solution (e.g., 83.5 $\mu$l) and one part of phosphatidylcholine solution (e.g., 41.5 $\mu$l) and 100 $\mu$l of 2,3-dihydroxyprmpyl 12-(7-nitro benzo[1,2,3] oxadiazol-4-ylamino)dodecanoate (NAG) solution (10 mg in 1 ml of chloroform) were pipetted together (final concentration in the test: 0.0375 mg of phospholipid/ml; 0.05 mg/NAG/ml). After removal of the chloroform, 20 ml of 25 mM TRIS/HCl, pH 7.4; 150 mM NaCl was added and two ultrasonic treatments were carried out using an ultrasonic probe (Branson Sonifier type II, standard microtip, 25 W): 1st treatment: setting 2, 2×1 min, in between 1 min each on ice; 2nd treatment: setting 4, 2×1 min, in between 1 min each on ice. During this procedure, the color of the substrate solution changed from yellow (extinction maximum 481 nm) to red (extinction maximum 550 nm) due to intercalation of NAG between the phospholipid molecules of the vesicles/micelles.

The free fatty acid forms no micelles or vesicles. Therefore a color change from red to yellow was observed during the removal of the fatty acid from the micelles/vesicles. Thus, the destruction of the micelles/vesicles and the enzyme activity of the lipase is measurable, either visually (at 481 nm, or at 550 nm), by means of the color change from red to yellow, with the aid of a cuvette photometer (e.g., DU-640 from Beckman (Munich)) or of a microtiter plate reader (e.g., Microβeta from Wallac (Turku, Finland)) or alternatively fluorimetrically with the aid of a phosphorimager (e.g., Storm 840 from Molecular Dynamics (Krefeld)), of a fluorescence scanner (e.g., DA-2 from Shimadzu (Osaka, Japan)), or of an image analysis process (e.g., ArrayScan from Molecular Devices (USA)) which is based on a CCD camera (charge-coupled device), which has an integrated circuit for the processing of electric and optical signals wherein the information is stored and transmitted in the form of electrical charges.

All these methods are preferably employed in combination with high-throughput screening (HTS). Further processes that are based on this concept are the measurement of the cytotoxicity of compounds and the action of detergents.

The invention also relates to a substrate prepared by the process described above and a substrate for use in a process for the identification of structures which favor the arrangement of aromatics to give charge-transfer complexes, preferably for the identification of phospholipid/lipid structures, particularly preferably of lipases/lipase inhibitors, as described above. The process can also be employed for the destruction of mono- or bilayer structures, which are curved (e.g., micelles or vesicles) or planar (e.g., artificially produced straight bilayers), which is accompanied by a color change. The color change can be monitored visually/optically or in a fluorimetrically measurable manner, as described above.

The invention further relates to a process for the preparation of the monoacylglyceride 2,3-dihydroxypropyl 12-(7-nitrobenzo[1,2,3]oxadiazol-4-ylamino)dodecanoate, where 12-aminolauric acid is first reacted with 7-chloro-4-nitrobenzo-2-oxa-1,3-diazole and the intermediate obtained is then reacted with 2,3-epoxypropanol in alcoholic solution at room temperature with addition of a base, such as alkali metal carbonate and alkali metal $C_{1-C4}$-alkanolate, preferably methanolate, such as sodium methanolate or potassium methanolate, and the monoacylglyceride 2,3-dihydroxypropyl 12-(7-nitrobenzo[1,2,3]oxadiazol-4-ylamino) dodecanoate itself.

The object of the invention is achieved by a process for the identification of lipases/lipase inhibitors whose presence produces a color change, comprising a) preparing a substrate as described above, b) incubating this substrate with a lipase (such as, for example, a HSL, monoglyceride lipase, diglyceride lipase, triglyceride lipase, LPL, pancreatic lipase, hepatic lipase, bacterial lipase, $PLA_2$, PLC, cholesterol esterase, preferably a HSL and a pancreatic lipase, particularly preferably a HSL), and c) determining the color change, e.g., visually/optically or fluorimetrically.

The invention further relates to lipases and lipase inhibitors that have been identified by the process described above.

The invention likewise relates to a process for determination of the activity of lipases/lipase inhibitors, where a substrate such as described above is prepared, this substrate is incubated with a lipase, and the rate of color change from red to yellow or conversely from yellow to red is determined and the activity is ascertained, for example, by means of an absorption measurement with a photometer or a fluorescence measurement with a fluorimeter.

A typical reaction is carried out at 30° C. for 60 min, for example in 1.5 ml Eppendorf vessels or 96-hole plates. 10 $\mu$l of a test substance (e.g., inhibitors of HSL) are introduced in assay buffer (25 mM TRIS/HCl, pH 7.4; 150 mM NaCl) in the presence of 16.6% DMSO. 180 $\mu$l of the substrate solution (20 $\mu$g/ml of phosphatidylcholine, 10 $\mu$g/ml of phosphatidylinositol, 50 $\mu$g/ml of NAG in assay buffer) are added. After a preincubation for 15 min at 30° C., 20 $\mu$l of HSL in assay buffer are pipetted in and the extinction is immediately measured (see above) at 481 nm in a cuvette photometer (0.5 ml cuvette) or microtiter plate reader. After a certain incubation time, which is variable and depends on the chosen enzyme concentration and can be between 2 and 240 minutes, in this case incubation at 30° C. for 60 min, the extinction is measured again. The increase in the extinction in the yellow region, in this case at 481 nm, is a measure of the enzyme activity.

Assay systems for identification of a lipase inhibitor or for determination of the activity of a lipase/lipase inhibitor are likewise a subject of the invention. They comprise a substrate such as described above, an ultrasonic device, and optionally a device for the visual/optical and/or fluorimetric determination of the color change from red to yellow or, in addition to a substrate as described above and an ultrasonic device, a device for determination of the rate of color change and a device for absorption or fluorescence measurement.

The assay system can also be present in the form of a kit, the assay being a lipase assay.

The kit contains a substrate as described above, optionally in an assay buffer, and a container for carrying out the test, such as an Eppendorf vessel or a microtiter plate, preferably a microtiter plate.

Further subjects of the invention relate to processes for determination of molecular transport/transfer systems, for measurement of the detergent action of compounds, or for investigation of the cytotoxicity of compounds (medicaments and the like) comprising a substrate as described above and a phospholipase, for example $PLA_2$ (from snake venom) or PLC (*Bacillus cereus*).

Transporters/transfer proteins are understood as meaning proteins which themselves recognize principal nutrients such as carbohydrates, lipids, and proteins and transport them through biological membranes or transfer them from a certain biological membrane to another. Transporters/transfer proteins, for example isolated from rat ileum, are functionally reconstituted (proteoliposomes) in phospholipid vesicles (liposomes) or incubated together with liposomes as soluble polypeptides and then added to a mixture of phospholipids and NBD-glyceride as described above and treated with ultrasound. The transport process or transfer process of the NBD-glyceride from the NBD-glyceride-containing micelles/vesicles into the lumen of the proteoliposomes with the aid of the transporters or into the membrane of the liposomes with the aid of the transfer proteins leads to the dissolution/destruction of the micelle structure and can in turn be monitored photometrically or fluorimetrically as described above.

The detergent action of chemical compounds is based on the direct destruction of the micelles/vesicles. As biological membranes are also constructed in this way, such compounds are usually cytotoxic. Destruction of micelles can easily be detected using the present process by means of the described color change.

Syntheses:

A few NBD-labeled fatty acids such as 12-(7-nitrobenzo[1,2,3]oxadiazol-4-ylamino)dodecanoic acid(1) are indeed commercially available, but expensive. Although the first experiments were also carried out with commercially obtainable material, it was possible to obtain compound (1) in good yields by reaction of 12-aminolauric acid with 4-chloro-7-nitrobenzo[1,2,5]oxadiazole in MeOH.

List of the compounds 1–9:

(1) 12-(7-nitrobenzo[1,2,3]oxadiazol-4-ylamino)dodecanoic acid
(2) 2,3-epoxypropanol

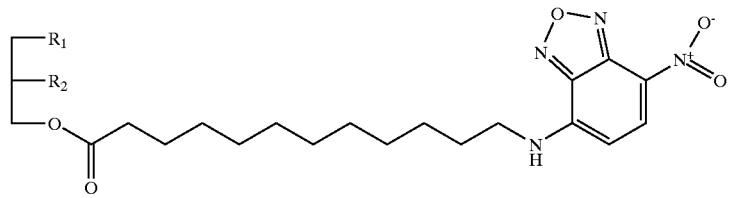

I

| Compound No. | Formula I: $R_1$ | Formula I: $R_2$ |
|---|---|---|
| (3) | OH | OH |
| (4) | OAc | OAc |
| (5) | $OOC(CH_2)_3CH_3$ | $OOC(CH_2)_3CH_3$ |
| (6) | $OOC(CH_2)_{14}CH_3$ | OH |
| (7) | $OOC(CH_2)_{14}CH_3$ | OAc |
| (8) | $O(CH_2)_{17}CH_3$ | $O(CH_2)_{17}CH_3$ |
| (9) | isopropylidene | isopropylidene |

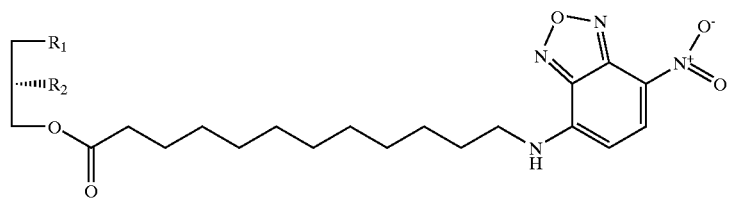

Ia

| Compound No. | Formula Ia: $R_1$ | Formula Ia: $R_2$ |
|---|---|---|
| (9a) | isopropylidene | isopropylidene |
| (3a) | OH | OH |

-continued

Ib

[Structure: R1, R2, O-C(=O)-(CH2)10-NH-[7-nitrobenzo[1,2,3]oxadiazol-4-yl]]

| Compound No. | Formula Ib: $R_1$ | Formula Ib: $R_2$ |
|---|---|---|
| (9b) | isopropylidene | isopropylidene |
| (3b) | OH | OH |

By nucleophilic addition of (1) to 2,3-epoxypropanol (2), it was possible to obtain the monoacylglyceride (3) in good yields. Compound (3) was then acylated in order to reach the triglycerides (4) and (5). The diacylglyceride (6) was obtained by esterification of (1) with palmitin. This compound was also reacted to give the corresponding triacylglyceride (7). The same method was used in order to react the glycerol diether (8) to give the pseudotriacylglyceride (9), wherein two acyl radicals are replaced by long-chain ethers.

All compounds synthesized proved to be substrates of lipases, preferably of HSL, but showed considerable activity differences. The "best" substrate of the lipases proved to be the monoacylglyceride (3). The introduction of further acyl groups, as in the compounds (4), (5), (6), and (7), led to a decrease in activity.

This can easily be explained by competition in the removal of the NBD acyl group by the newly introduced acyl radicals. In order to confirm this hypothesis, a pseudotriacylglyceride (9) was synthesized wherein two acyl groups are replaced by hexadecyl ether units. These cannot be removed from the lipases and should therefore not compete with the NBD fatty acid ester. In biological tests, this compound indeed proved to be a substrate, but with low activity. Obviously, in addition to the catalytic region, the lipases have an extended hydrophobic binding region accessible to the long-chain ether groups, such that the addition of the fatty acid unit is impeded.

As the monoacylglyceride (3) proved to be a good substrate of the lipases, it was investigated whether there is a regioselective preference for position 1 or 3. For these investigations, the enantiomeric regioisomers (3a) and (3b) were synthesized.

The synthesis of the enantiomers (3a, b) starts from D- and L-1,2-O-isopropylideneglycerol, which is esterified with the NBD-labeled fatty acid (1) by dicyclohexylcarbodiimide (DCC) activation. The protective group was removed using 1 N methanolic HCl. Both compounds showed identical biological activity, such that the use of enantiomerically pure compound promises no advantage.

EXAMPLE 1

12-(7-Nitrobenzo[1,2,3]oxadiazol-4-ylamino) dodecanoic acid (Compound (1))

30% strength sodium methanolate solution (14.5 ml, 76 mmol) is added with stirring to a solution of 12-aminolauric acid (18 g, 83.7 mmol) in MeOH (300 ml). After 5 minutes, the reaction mixture becomes clear and a solution of 7-chloro-4-nitrobenzo-2-oxa-1,3-diazole (15 g, 75 mmol) in MeOH (300 ml) is added. The reaction mixture, which immediately becomes dark, is stirred for 18 h at 25° C. 1 M methanolic HCl (100 ml, 100 mmol) is then added and the solvent is distilled off in vacuo. The residue is taken up in MeOH, the mixture is filtered through silica gel, the filtrate is concentrated to dryness, and the residue is purified by flash chromatography (1:1 toluene/EtOAc). Compound (1) is obtained as a red solid (26.4 g, 93%).

$R_f$: 0.16 (1:1 toluene/EtOAc).

$^1$H-NMR (250 MHz, CDCl$_3$): δ 8.5 (d, 1H, ArH), 6.35 (m, 1H, NH), 6.18 (d, 1H, ArH), 3.48 (dt, 2H, $C\overline{H}_2NH_2$), 2.36 (t, 2H, $C\overline{H}_2COOH$), 1.9–1.2 (m, 18H, 9 CH$_2$). MS) (ESI-MS): 379.2 (M+1).

EXAMPLE 2

2,3-Dihydroxypropyl 12-(7-nitrobenzo[1,2,3] oxadiazol-4-ylamino) dodecanoate (Compound (3))

A solution of compound (1) (12 g, 31.7 mmol) and 2,3-epoxypropanol (50 ml) in isopropanol (50 ml) is stirred at 50° C. for 16 h. The solvent is distilled off in vacuo, and the residue is dried at 0.01 torr and purified by flash chromatography (diisopropyl ether, ether, EtOAc). Compound (3) is obtained as a red oil (10.3 g, 71.8%).

$R_f$: 0.18 (1:1 toluene/EtOAc); $R_f$: 0.5 (30:5:1 CH$_2$Cl$_2$/MeOH/NH$_3$), which crystallized from EtOAc/diethyl ether.

$^1$H-NMR (250 MHz, CDCl$_3$): δ 8.5 (d, 1H, ArH), 6.35 (m, 1H, NH), 6.18 (d, 1H, ArH), 4.19 (dd, 2H, H-1, H-1'), 3.94 (m, 1H, H-2), 3.65 (dd, 2H, H-3, H-3'), 3.48 (dt, 2H, $C\overline{H}_2NH_2$), 2.35 (t, 2H, $C\overline{H}_2COOH$), 1.8 (m, 2H, CH$_2$), 1.6 (m, 2H, CH$_2$), 1.27–1.15 (m, 14H, 7 CH$_2$). MS (ESI-MS): 453.4 (M+1).

EXAMPLE 3

(S)-2,2-Dimethyl[1,3]dioxolan-4-ylmethyl 12-(7-nitrobenzo[1,2,5]oxadiazol-4-ylamino)dodecanoate (Compound (9a))

A solution of compound (1) (60 mg, 159 μmol) in CH$_2$Cl$_2$ (2 ml) is treated with DCC (160 mg, 770 μmol) and stirred at 25° C. for 30 min. A solution of (R)-(2,2-dimethyl[1,3] dioxolan-4-yl)methanol (100 mg, 760 μmol) and dimethylaminopyridine (94 mg, 770 μmol) in CH$_2$Cl$_2$ (2 ml) is then added and the reaction solution is stirred for a further 4 h at 25° C. The solvent is distilled off in vacuo and the residue is purified by flash chromatography (15:1 toluene/EtOAc). Compound (9a) is obtained as a yellow fluorescent oil (46 mg, 58%).

$R_f$: 0.29 (4:1 toluene/EtOAc).

$^1$H-NMR (CDCl$_3$): δ 8.5 (d, 1H, aromat.), 6.2 (m, 1H, NH), 6.16 (d, 1H, aromat.), 4.31 (m, 1H), 4.1 (m, 3H), 3.73 (dd, 1H), 3.48 (dt, 2H, $C\overline{H}_2NH_2$), 2.35 (t, 2H, CO—$C\overline{H}_2$), 2.0–1.2 (m, 18H, 9 CH$_2$), 1.42 (s, 3H, CMe$_2$), 1.37 (s, 3H, CMe$_2$).

EXAMPLE 4

(R)-2,2-Dimethyl[1,3]dioxolan-4-ylmethyl 12-(7-nitrobenzo[1,2,5]oxadiazol-4-ylamino)dodecanoate (Compound (9b))

Compound (9b) is prepared as described for compound (9a). Compound (9b) is obtained as a yellow fluorescent oil (51.4 mg, 65%).

$R_f$: 0.29 (4:1 toluene/EtOAc).

$^1$H-NMR (CDCl$_3$): δ 8.5 (d, 1H, ArH), 6.2 (m, 1H, NH), 6.16 (d, 1H, ArH), 4.31 (m, 1H), 4.1 (m, 3H), 3.73 (dd, 1H), 3.48 (dt, 2H, C$\overline{H}_2$NH$_2$), 2.32 (t, 2H, CO—C$\overline{H}_2$), 2.0–1.2 (m, 18H, 9 C$\overline{H}_2$), 1.42 (s, 3H, CMe$_2$), 1.37 (s, 3H, CMe$_2$).

EXAMPLE 5

(S)-2,3-Dihydroxypropyl 12-(7-nitrobenzo[1,2,5]oxadiazol-4-ylamino) dodecanoate and (R)-2,3-dihydroxypropyl 12-(7-nitrobenzo[1,2,5]oxadiazol-4-ylamino)dodecanoate (Compound (3b))

Methanolic HCl (1 M, 200 μl) is added to a solution of 13.9 mg (28.2 μmol) of compound (9a) or 17.8 mg (36.1 μmol) of compound (9b) in 25 ml of methanol and the mixture is stirred for 1.5 h at 25° C. The solvent is distilled off in vacuo and the residue is purified by flash chromatography (2:1, 1:1 toluene/EtOAc). The fatty acid esters (3a) and (3b) are obtained in a yield of 10.5 mg (82%), and 9.3 mg (57%) respectively. $^1$H-NMR (CDCl$_3$) data and mass spectra are identical to compound (3).

EXAMPLE 6

2-Acetoxy-3-[12-(7-nitrobenzo[1,2,5]oxadiazol-4-ylamino)-dodecanoyloxy]propyl acetate (Compound (4))

Compound (3) (12 mg, 26.5 μmol) is acetylated in 2:1 pyridine/acetic anhydride (3 ml). After 8 h, the mixture is concentrated to dryness and the residue is purified by flash chromatography (1:2 toluene/EtOAc). Compound (4) is obtained as a yellow fluorescent oil (13 mg, 91%).

$R_f$: 0.66 (1:1 toluene/EtOAc).

$^1$H-NMR (250 MHz, CDCl$_3$): δ 8.5 (d, 1H, ArH), 6.3 (m, 1H, NH), 6.18 (d, 1H, ArH), 5.24 (m, 1H), 4.92 (m, 1H), 4.34 (m) 4.28, 4.16, 3.48 (dt, 2H, C$\overline{H}_2$NH$_2$), 2.32 (CH$_2$COO), 2.1 (2 s, 6H, 2 OAc), 2.0–1.0 (m, 18H, 9 CH$_2$). MS (ESI-MS): 537.4 (M+1)

EXAMPLE 7

2-Hexanoyloxy-3-[12-(7-nitrobenzo[1,2,5]oxadiazol-4-ylamino)-dodecanoyloxy]propyl hexanoate (Compound (5))

Hexanoic anhydride (100 μl) is added to a solution of compound (2) (5 mg, 11 μmol) in pyridine (300 μl) and the reaction mixture is allowed to stand at 25° C. for 16 h. The solvent is distilled off in vacuo and the residue is purified by flash chromatography (9:1 toluene/EtOAc). Compound (5) is obtained as a yellow fluorescent oil (1.8 mg, 25%).

$R_f$: 0.73 (1:1 toluene/EtOAc).

$^1$H-NMR (250 MHz, CDCl$_3$): δ 8.5 (d, 1H, ArH), 6.25 (m, 1H, NH), 6.18 (d, 1H, ArH), 5.26 (m, 1H, H-2), 4.29 (dd, 2H, H-3, H-3'), 4.15 (dd, 2H, H-1, H-1'), 3.46(dt, 2H, C$\overline{H}_2$—NH), 2.34 (t, 6H, 3 C$\overline{H}_2$COO), 1.63–1.2 (m, 12H, 6 CH$_2$), 0.88 (m, 6H, 2 CH$_3$) MS (ESI-MS): 649.5 (M+1).

EXAMPLE 8

2-Hydroxy-3-[12-(7-nitrobenzo[1,2,5]oxadiazol-4-ylamino)-odecanoyloxy]propyl hexadecanoate (Compound (6))

A solution of compound (1) (25 mg, 66 μmol), 4dimethylaminopyridine (9 mg, 73 μmol), and 1,1 carbonyldiimidazole (15 mg, 73 μmol) in CH$_2$Cl$_2$ (5 ml) is stirred at 25° C. for 30 min. The solvent is distilled off in vacuo and the residue is purified by flash chromatography (9:1 toluene/EtOAc). Compound (6) is obtained as a yellow fluorescent oil (9.5 mg, 21%).

$R_f$: 0.25 (5:1 toluene/EtOAc).

$^1$H-NMR (250 MHz, CDCl$_3$): δ 8.54 (d, 1H, ArH), 6.3 (m, 1H, NH), 6.19 (d, 1H, ArH), 4.20 (dd, 2H, H-1, H-1'), 4.15 (dd, 2H, H-3, H-3'), 4.12 (m, 1H, H-2), 3.5 (dt, 2H, C$\overline{H}_2$—NH), 2.36 (t, 4H, 2 C$\overline{H}_2$COO), 1.82 (m, 2H, CH$_2$—CH$_2$—NH), 1.63 (m, 4H, 2 CH$_2$CH$_2$COO), 1.47 (m, 2H, CH$_2$—(CH$_2$)$_2$—NH), 1.31–1.26 (m, 22H, 11 CH$_2$), 1.287 (m, 2H, CH$_2$), 1.26 (m, 2H, CH$_2$), (m, 4H, 2 CH$_2$CH$_2$CH$_2$COO), 1.31–1.26 (m, 1.3 (m, 2H, CH$_2$), 1.26 (m, 2H, CH$_2$), 0.89 (t, 3H, CH$_3$). MS (ESI-MS): 649.5 (M+1)

EXAMPLE 9

2-Acetyloxy-3-[12-(7-nitrobenzo[1,2,5]oxadiazol-4-ylamino)-dodecanoyloxy]propyl hexadecanoate (Compound (7))

Compound (6) (6 mg, 8.7 μmol) is acetylated and worked up as described for compound (4). The crude product is purified by flash chromatography (9:1 toluene/EtOAc). Compound (7) is obtained as a yellow fluorescent oil (5.1 mg, 95%).

$R_f$: 0.71(5:1 toluene/EtOAc).

$^1$H-NMR (250 MHz, CDCl$_3$): δ 8.5 (d, 1H, ArH), 6.25 (m, 1H, NH), 6.17 (d, 1H, ArH), 5.25 (m, 1H, H-2), 4.27 (dd, 2H, H-1, H-3), 4.15 (dd, 2H, H-1', H-3'), 3.73 (dt 4H, CH$_2$NH), 2.3 (t, 2H, CH$_2$COO), 2.08 (s, 3H, OAc), 1.8 (m, 2H, CH$_2$—CH$_2$—NH), 1.6 (1.6 m, 8H, 4 CH$_2$), 1.4–1 (m, 32H, 16 CH$_2$), 0.85 (t, 3H, CH$_3$). MS (FAB-MS): 739 (M+1).

EXAMPLE 10

2,3-bis-Octadecyloxy-propyl 12-(7-nitrobenzo[1,2,5]oxadiazol-4-ylamino)dodecanoate (Compound (8))

2,3-bis-Octadecyloxypropan-1-ol (5 mg, 8.37 μmol) is added to a solution of compound (1) (3 mg, 7.9 μmol), dimethylaminopyridine (5 mg, 41 μmol), and DCC (5 mg, 24 μmol) in CH$_2$Cl$_2$. The reaction mixture is stirred at 25° C. for 2 h, the solvent is distilled off in vacuo, and the residue is purified by flash chromatography (2:1 petroleumether/diethyl ether). Compound (8) is obtained as a yellow fluorescent oil (3.5 mg, 46%).

$R_f$: 0.55 (3:7 diethyl ether/petroleum ether).

MS (FAB-MS): 957.8 (M+1).

Enzyme Preparation

Preparation of the Partially Purified HSL:

Isolated rat fat cells are obtained from epididymal fatty tissue from untreated male rats (Wistar, 220–250 g) by collagenase treatment according to published processes. The fat cells from 10 rats are washed three times by flotation with 50 ml each of homogenization buffer (25 ml TRIS/HCl, pH 7.4, 0.25 M sucrose, 1 mM ethylenediamine-N,N,N',N'-tetraacetic acid (EDTA), 1 mM dithiothreitol (DTT), 10 μg/ml of leupeptin, 10 μg/ml of antipain, 20 μg/ml of pepstatin) and finally taken up in 10 ml of homogenization buffer. The fat cells are homogenized in a Teflon-in-glass homogenizer (Braun-Melsungen) by 10 strokes at 1500 rpm and 15° C. The homogenizate is centrifuged (Sorvall SM24 tubes, 5000 rpm, 10 min, 4° C.). The bottom layer between the overlying fatty layer and the pellet is removed and the centrifugation is repeated. The bottom layer resulting from this is centrifuged again (Sorvall SM24 tubes, 20,000 rpm, 45 min, 4° C.). The bottom layer is removed and treated with 1 g of heparin-Sepharose (Pharmacia Biotech, CL-6B, washed 5 times with 25 mM TRIS/HCl, pH 7.4, 150 mM NaCl). After incubation for 60 min at 4° C. (shake at intervals of 15 min), the batch is centrifuged (Sorvall SM24 tubes, 3000 rpm, 10 min, 4° C.). The supernatant is brought to pH 5.2 by addition of glacial acetic acid and incubated at 4° C. for 30 min. The precipitates are collected by centrifugation (Sorvall SS34, 12,000 rpm, 10 min, 4° C.) and suspended in 2.5 ml of 20 mM TRIS/HCl, pH 7.0, 1 mM EDTA, 65 mM NaCl, 13% sucrose, 1 mM DTT, 10 $\mu$g/ml of leupeptin/pepstatin/antipain. The suspension is dialyzed overnight at 4° C. against 25 mM TRIS/HCl, pH 7.4, 50% glycerol, 1 mM DTT, and 10 $\mu$g/ml of leupeptin, pepstatin, and antipain and then applied to a hydroxylapatite column (0.1 g per 1 ml of suspension, equilibrated with 10 mM potassium phosphate, pH 7.0, 30% glycerol, 1 mM DTT). The column is washed with four volumes of equilibration buffer at a flow rate of 20 to 30 ml/h. The HSL is eluted with a volume of equilibration buffer which contains 0.5 M potassium phosphate, then dialyzed (see above) and concentrated 5 to 10 times by ultrafiltration (Amicon Diaflo PM 10 filter) at 4° C. The partially purified HSL can be stored at $-70°$ C. for 4 to 6 weeks.

Preparation of the NAG (NBD-monoacylglyceride) Substrate:

6 mg of phosphatidylcholine and 6 mg of phosphatidylinositol are dissolved in 1 ml of chloroform each. 10 mg of NAG are dissolved in 1 ml of chloroform. Two parts of phosphatidylinositol solution (e.g., 83.5 $\mu$l) and one part of phosphatidylcholine solution (e.g., 41.5 $\mu$l) and 100 $\mu$l of NAG solution are pipetted together into plastic scintillation containers (final concentration in the test: 0.0375 mg of phospholipid/ml; 0.05 mg/NAG/ml). The chloroform (225 $\mu$l total volume) is completely removed by overblowing with a stream of $N_2$. The dried substrate can be stored at 4° C. for up to three days. For the preparation of the phospholipid vesicles/micelles having intercalated NAG (on the test day), the dried substrate is taken up in 20 ml of assay buffer (25 mM TRIS/HCl, pH 7.4; 150 mM NaCl) and two ultrasonic treatments with an ultrasonic probe (Branson Sonifier type 11, standard microtip): 1st treatment setting 2, 2×1 min, in between in each case 1 min on ice; 2nd treatment setting 4, 2×1 min, in between in each case 1 min on ice. During this procedure, the color of the substrate solution changed from yellow (extinction maximum 481 nm) to red (extinction maximum 550 nm) due to intercalation of NAG between the phospholipid molecules of the vesicles/micelles. Before use as a substrate (within the next 2 h), the solution is additionally incubated on ice for 15 min.

Indirect NAG Assay:

The assay is carried out at 30° C. for 60 min in 1.5 ml Eppendorf vessels or 96-hole plates. To find inhibitors of HSL, 10 $\mu$l of the test substance in assay buffer (25 mM TRIS/HCl, pH 7.4; 150 mM NaCl) are introduced in the presence of 16.6% DMSO. 180 $\mu$l of the substrate solution (20 $\mu$g/ml of phosphatidylcholine, 10 $\mu$g/ml of phosphafidylinositol, 50 $\mu$g/ml of NAG in assay buffer) are added. After a preincubation for 15 min at 30° C., 20 $\mu$l of the enzyme solution in assay buffer (diluted 1 to 4 times) are pipetted in and the extinction is immediately measured at 480 nm in a cuvette photometer (0.5 ml cuvette) or microtiter plate reader (microleta, Wallac). After incubation at 30° C. for 60 min, the extinction is measured again. The increase in the extinction at 480 nm is a measure of the enzyme activity. Under standard conditions, 20 $\mu$g of partially purified HSL leads to an extinction change of 4000 arb. units.

Direct NAG Assay:

Alternatively to the measurement of the extinction change of the substrate solution, the products of the HSL reaction are investigated by phase separation/thin-layer chromatography. For this, the incubation batch (200 $\mu$l total volume, see indirect NAG assay) is mixed in 2 ml Eppendorf vessels with 1.3 ml of methanol/chloroform/heptane (10:9:7) and then with 0.4 ml of 0.1 M NaOH. After intensive mixing (10 sec), the phase separation is initiated by centrifugation (800×g, 20 min, room temperature). Equivalent volumes (e.g., 0.4 ml) are taken from the aqueous upper phase and the extinction is determined photometrically at 481 nm. For thin-layer chromatography, the aqueous phase is dried (SpeedVac) and then taken up in 50 $\mu$l of tetrahydrofuran. 5 $\mu$l samples are applied to silica gel Si-60 plates (Merck, Darmstadt). The chromatography is carried out using 78 ml of diethyl ether/22 ml of petroleum ether/1 ml of glacial acetic acid as an eluent. The amount of released fluorescent NBD fatty acid is determined by phosphorimaging (Molecular Dynamics, Storm 840 and ImageQuant software) at an excitation wavelength of 460 nm and emission wavelength of 540–560 nm.

TAG Assay:

For the preparation of the substrate, 25–50 $\mu$Ci of [$^3$H] trioleoylglycerol (TAG)(in toluene), 6.8 $\mu$Mol of unlabeled trioleoylglycerol, and 0.6 mg of phospholipids (phosphatidylcholine/phosphatidylinositol 3:1 w/v) are mixed, dried over $N_2$, and then taken up in 2 ml of 0.1 M potassium dihydrogenphosphate/potassium phosphate buffer (KP$_i$)(pH 7.0) by ultrasonic treatment (Branson 250, microtip, setting 1–2, 2×1 min at a 1 min interval). After addition of 1 ml KP$_i$ and fresh ultrasonic treatment (4×30 sec on ice at 30 sec intervals), 1 ml of 20% bovine serum albumin (BSA)(in KP$_i$) is added (final concentration of trioleoylglycerol 1.7 mM). For the reaction, 100 $\mu$l of substrate solution are pipetted into 100 $\mu$l of HSL solution (HSL prepared as above, diluted in 20 mM KP$_i$, pH 7.0, 1 mM EDTA, 1 mM DTT, 0.02% BSA, 20 $\mu$g/ml of pepstafin, 10 $\mu$g/ml of leupeptin) and incubated at 37° C. for 30 min. After addition of 3.25 ml of methanol/chloroform/heptane (10:9:7) and of 1.05 ml of 0.1 M $K_2CO_3$, 0.1 M boric acid (pH 10.5), the batch is well mixed and finally centrifuged (800×g, 20 min). After phase separation, one equivalent of the upper phase (1 ml) is taken and the radioactivity is determined by liquid scintillation measurement.

PNPB Assay:

10 $\mu$l of p-nitrophenyl butyrate (PNPB)(2 mM in acetonitrile), 890 $\mu$l of 0.1 M KP$_i$ (pH 7.25), 0.9% NaCl, 1 mM DTT, and 100 $\mu$l of HSL (prepared as above, diluted in this buffer) are incubated at 37° C. for 10 min. After addition of 3.25 ml of methanol/chloroform/heptane (10:9:7, w/v) and vigorous shaking, the batch is centrifuged (800×g, 20 min) and incubated at 42° C. for 3 min. An equivalent volume of the upper phase is then taken and the absorption is determined at 400 nm.

Tributyrin Assay:

For the preparation of the substrate, 5 $\mu$Ci of [1-$^{14}$C] tributyrin (in toluene) are added to 1 ml of 20 mM unlabeled tributyrin (in acetonitrile). 10 $\mu$l of this substrate solution are incubated at 37° C. for 30 min with 390 $\mu$l of 0.1 M KP$_i$ (pH 7.25), 0.9% NaCl, 1 mM DTT, 5 2% BSA, and 100 $\mu$l of HSL (prepared as above, diluted in this buffer). After addition of 3.25 ml of methanol/chloroform/heptane (10:9:7, w/v) and of 1 ml of 0.1 M NaOH, the batch is vigorously mixed and finally centrifuged (800×g, 20 min). An equivalent volume (1 ml) of the upper phase is taken and the radioactivity is determined by liquid scintillation measurement.

Analysis:

Substances are customarily tested in four independent batches. The inhibition of the enzymatic activity of the HSL by a test substance is determined by comparison with an uninhibited control reaction. The $IC_{50}$ value is calculated by means of an inhibition curve using at least 10 concentrations of the test substance. For the analysis of the data, the software package GRAPHIT, Elsevier-BIOSOFT (version 3.0) is used.

EXAMPLES

Example 1

Kinetics of the Cleavage of NAG by HSL

NAG (0.05 mg/ml) is incubated with the indicated amounts of partially purified HSL protein (temperature-controlled photometer) and the extinction at 481 nm in the (lacuna) is determined at specific times. For inactivation, the HSL is incubated at 100° C. for 15 min. (n =8, mean : SD). Result: Up to an amount of protein of 20 µg, the reaction proceeds linearly up to 60 min. The extinction difference is in this case 0.8–0.9 OD. In the case of smaller amounts of protein, linearity is afforded up to 180 min.

Example 1

Kinetics of the Cleavage of NAG by HSL

TABLE 1

| | Increase in the absorption at 481 nm (arb. units) | | | | | |
|---|---|---|---|---|---|---|
| Time, min | Without HSL | Inactive HSL | HSL, 5 µg | HSL, 10 µg | HSL, 20 µg | HSL, 40 µg |
| 0 | 0 | 0 | 0 | 0 | 0 | 0 |
| 1 | 5 ± 2 | 4 ± 1 | 12 ± 2 | 19 ± 4 | 5 ± 7 | 91 ± 14 |
| 2 | 7 ± 2 | 5 ± 2 | 23 ± 4 | 51 ± 9 | 78 ± 12 | 89 ± 32 |
| 5 | 13 ± 4 | 10 ± 4 | 45 ± 9 | 102 ± 19 | 193 ± 36 | 395 ± 62 |
| 10 | 15 ± 3 | 12 ± 3 | 105 ± 18 | 185 ± 26 | 423 ± 62 | 784 ± 88 |
| 15 | 17 ± 5 | 15 ± 4 | 155 ± 20 | 288 ± 39 | 617 ± 70 | 1060 ± 144 |
| 20 | 19 ± 5 | 20 ± 5 | 219 ± 31 | 395 ± 36 | 865 ± 93 | 477 ± 182 |
| 30 | 19 ± 6 | 24 ± 7 | 295 ± 47 | 517 ± 67 | 1143 ± 216 | 2249 ± 286 |
| 45 | 23 ± 6 | 32 ± 6 | 453 ± 52 | 830 ± 57 | 1877 ± 206 | 2968 ± 321 |
| 60 | 25 ± 8 | 37 ± 9 | 677 ± 70 | 1179 ± 110 | 2510 ± 295 | 4065 ± 399 |
| 75 | 28 ± 9 | 39 ± 10 | 831 ± 92 | 1487 ± 104 | 3067 ± 310 | 4834 ± 462 |
| 90 | 31 ± 8 | 41 ± 13 | 995 ± 82 | 1844 ± 130 | 3527 ± 188 | 5472 ± 813 |
| 120 | 35 ± 7 | 45 ± 11 | 1455 ± 102 | 2745 ± 195 | 4941 ± 410 | 5702 ± 531 |
| 180 | 39 ± 11 | 52 ± 15 | 1937 ± 121 | 3521 ± 254 | 5712 ± 399 | 5961 ± 560 |

Example 2

Dependence of the Cleavage of NAG on the Amount of HSL

NAG (0.05 mg/ml) is incubated with the indicated amounts of partially purified HSL protin for 60 min. The increase in the extinction at 481 nm (formation of the free NBD fatty acid as a product of the HSL reaction=indirect NAG assay) or the decrease in the extinction at 550 nm (consumption of NAG as a substrate of the HSL reaction) is determined in aliquots of the reaction batches. Alternatively, further aliquots are extracted with methanol/chloroform and the released NBD fatty acid (12-(7-nitrobenzo[2,3]oxadiazol-4-ylamino)-dodecanoic acid (NBD-FA)) contained in the organic phase is determined (=direct NAG assay) (n=6, mean±SD) by TLC analysis and fluorimetry (phosphorimager Storm 840, Molecular Dynamics).

Results: Up to an amount of protein of 20 µg the reaction proceeds linearly with respect to product formation (extinction increase at 481 nm or occurrence of free NBD fatty acid according to TLC analysis) and with respect to the consumption of substrate (extinction decrease at 550 nm). The agreement between indirect and direct NAG assay supports the analysis of the cleavage of NAG in the indirect assay.

Example 2

Dependence of the Cleavage of NAG on the Amount of HSL

TABLE 2

| | Absorption change (arb. units) | | |
|---|---|---|---|
| Amount of HSL, µg | Increase, 481 nm | Decrease, 550 nm | Released NBD-FA, 550 nm |
| 0 | 0 | 885 ± 80 | 0 |
| 1 | 156 ± 21 | 866 ± 94 | 17 ± 2 |
| 2 | 347 ± 40 | 841 ± 78 | 44 ± 5 |
| 5 | 791 ± 88 | 779 ± 82 | 103 ± 11 |
| 7.5 | 1066 ± 120 | 759 ± 69 | 157 ± 21 |
| 10 | 1255 ± 141 | 650 ± 61 | 215 ± 24 |
| 15 | 2351 ± 205 | 540 ± 55 | 320 ± 29 |
| 20 | 2867 ± 199 | 287 ± 51 | 432 ± 53 |

TABLE 2-continued

| | Absorption change (arb. units) | | |
|---|---|---|---|
| Amount of HSL, µg | Increase, 481 nm | Decrease, 550 nm | Released NBD-FA, 550 nm |
| 25 | 3428 ± 270 | 198 ± 44 | 544 ± 61 |
| 30 | 3973 ± 244 | 115 ± 35 | 616 ± 56 |
| 40 | 4623 ± 511 | 91 ± 19 | 693 ± 67 |

TABLE 2-continued

| | Absorption change (arb. units) | | |
|---|---|---|---|
| Amount of HSL, µg | Increase, 481 nm | Decrease, 550 nm | Released NBD-FA, 550 nm |
| 60 | 5466 ± 602 | 62 ± 17 | 733 ± 80 |
| 80 | 5913 ± 485 | 54 ± 15 | 746 ± 98 |

Different amounts of NAG (with a constant ratio to the phospholipids) are incubated for 60 minutes with the indicated amounts of partially purified HSL and the extinction is then determined at 481 nm (n=5, mean±SD).

Result with all three amounts of enzyme, the cleavage rate exhibits the course of a typical saturation curve. On account of the enzymatic peculiarity of the HSL reaction ("two-dimensional" substrate presentation, "interfacial activation"), however, an approximately linear dependence can be determined only with 5 µg of protein and the lowest substrate concentrations. The combination of 20 µg of protein and 0.05 mg/ml of NAG represents a rational compromise between substrate dependence and signal strength (OD 0.6 to 0.7).

Example 3

Dependence of the Cleavage of NAG by HSL on the Substrate Concentration

TABLE 3

| | Increase in the absorption at 481 nm (arb. units) | | |
|---|---|---|---|
| NAG, mg/ml | HSL, 5 µg | HSL, 20 µg | HSL, 40 µg |
| 0.002 | 61 ± 9 | 194 ± 23 | 525 ± 77 |
| 0.005 | 109 ± 17 | 342 ± 58 | 1420 ± 122 |
| 0.01 | 227 ± 31 | 852 ± 77 | 2745 ± 264 |
| 0.02 | 388 ± 45 | 1758 ± 195 | 6705 ± 532 |
| 0.05 | 705 ± 61 | 3002 ± 409 | 11547 ± 912 |
| 0.075 | 1121 ± 107 | 768 ± 502 | 15502 ± 1077 |
| 0.1 | 1521 ± 119 | 6124 ± 577 | 19223 ± 1599 |
| 0.15 | 1983 ± 155 | 7544 ± 603 | 26730 ± 2069 |
| 0.2 | 2242 ± 186 | 8898 ± 961 | 31641 ± 2304 |
| 0.3 | 2489 ± 213 | 9734 ± 825 | 35953 ± 3355 |

Example 4

Dependence of the Cleavage of NAG by HSL on the Ratio of NAG and Phospholipids

NAG (0.05 mg/ml) is prepared as a substrate by ultrasonic treatment using different amounts of phospholipids (total amounts) with the indicated ratios of phosphatidylinositol (PI) to phosphatidylcholine (PC) and then incubated with partially purified HSL (20 µg) for 60 min. The increase in the extinction at 481 nm is determined (n=4, mean±SD).

Result: The enzyme rate is greatest with a PI/PC ratio (according to weight) of 3:1 and 0.0375 to 0.075 total phospholipid. The pronounced optimum course for the total concentration of the phospholipids and for their composition supports the importance of the presentation of the substrates of HSL (in this case NAG) in phospholipid vesicles and/or micelles or the formation of a monolayer of phospholipids on the (neutral) core of the substrate.

Example 4

Dependence of the Cleavage of NAG by HSL on the Ratio of NAG and Phospholipids

TABLE 4

| | Increase in the absorption at 481 nm (arb. units) | | |
|---|---|---|---|
| PI/PC, mg/ml | PI:PC 3:1 | PI:PC 1:1 | PI:PC 1:3 |
| 0 | 173 ± 42 | 134 ± 23 | 89 ± 12 |
| 0.009 | 1437 ± 132 | 548 ± 76 | 289 ± 77 |
| 0.018 | 2610 ± 306 | 1430 ± 188 | 692 ± 94 |
| 0.025 | 2980 ± 254 | 1879 ± 205 | 1158 ± 121 |
| 0.0375 | 3144 ± 277 | 1649 ± 170 | 1230 ± 105 |
| 0.075 | 3365 ± 402 | 1138 ± 125 | 1679 ± 143 |
| 0.15 | 2108 ± 256 | 745 ± 97 | 912 ± 103 |
| 0.3 | 913 ± 102 | 335 ± 47 | 427 ± 56 |

Example 5

Comparison of the Indirect/direct NAG Assay with a Conventional HSL Assay by Means of the Determination of the $IC_{50}$ Values for Various Inhibitors NAG (0.05 mg/ml) is incubated with 20 µg of partially purified HSL for 60 min in the presence of different concentrations (0.1 to 100 µM) of various substances. The extinction is determined at 481 nm in aliquots of the batches (indirect assay) or the NBD-FA released is extracted by chloroform/methanol and determined by TLC analysis and fluorimetry (direct assay). Alternatively, TAG is incubated with partially purified HSL according to published conditions and the radiolabeled oleate released is determined by liquid scintillation measurement after extraction with chloroform/methanol. The $IC_{50}$ values are determined from the inhibition curves (n=6, mean±SD).

Result: For all substances tested, typically sigmoidal inhibition curves were determined using the three processes. In the indirect/direct NAG assay (extinction increase at 481 nm/release of the NBD fatty acid), the $IC_{50}$ values were generally lower by a factor of 4 to 10 compared with the cleavage of trioleoylglycerol by HSL; the order of the inhibitors (according to their $IC_{50}$ values), however, is identical for all three processes. This confirms published findings that the action of inhibitors of HSL depends on the nature of the substrate and the substrate presentation. Moreover, the effective substrate concentrations (NAG and trioleoylglyceride) can also differ between the two assays (barely determinable on account of the substrate preparation as vesicles or micelles) and thus explain these differences in the case of competitive inhibitors. The nearly identical $IC_{50}$ values, which were determined according to the change in extinction and the NBD fatty acid release, propose cleavage of NAG by HSL and thus release of NBD fatty acid as a cause of the increase in extinction at 481 nm, i.e., the NAG assay detects the lipolytic cleavage of lipids.

Example 5

Comparison of the Indirect/direct NAG Assay with a Conventional HSL Assay by Means of the Determination of the $IC_{50}$ Values for Various Inhibitors

TABLE 5

| | $IC_{50}$, µM | | |
|---|---|---|---|
| Compound | NAG assay | NBD-FA released | TAG assay |
| 1 | 0.78 ± 0.24 | 0.78 ± 0.15 | 5.21 ± 1.44 |
| 2 | 0.75 ± 0.18 | 0.81 ± 0.27 | 12.12 ± 3.20 |
| 3 | 1.52 ± 0.33 | 1.02 ± 0.25 | 15.34 ± 2.43 |
| 4 | 2.45 ± 0.41 | 2.98 ± 0.49 | 18.25 ± 3.54 |
| 5 | 2.79 ± 0.59 | 3.58 ± 0.39 | 18.95 ± 2.31 |
| 6 | 3.42 ± 0.78 | 4.45 ± 0.22 | 21.45 ± 3.06 |
| 7 | 3.82 ± 0.61 | 4.51 ± 0.34 | 33.13 ± 2.88 |
| 8 | 4.29 ± 0.58 | 5.09 ± 0.94 | 35.94 ± 3.18 |
| 9 | 6.37 ± 0.72 | 6.94 ± 0.55 | 39.82 ± 2.95 |
| 10 | 7.51 ± 1.22 | 7.77 ± 1.19 | 47.85 ± 4.12 |
| 11 | 17.94 ± 2.15 | 21.33 ± 2.83 | 78.91 ± 5.66 |
| 12 | 22.38 ± 2.47 | 26.10 ± 3.82 | 116.34 ± 9.42 |

Example 6

Comparison of the Indirect NAG Assay with the Assays for TAG, PNPB, and Tributyrin NAG (0.05/ml) is incubated with 20 µg of partially purified HSL for 60 min in the presence of different concentrations (0.1 to 100 µM) of various substances. The extinction at 481 nm is determined in aliquots of the batches (indirect assay). Alternatively, TAG, PNPB, or [$^{14}$C] tributyrin is incubated with partially purified HSL and the radiolabled oleate, p-nitrophenol, or butyrate released is determined by liquid scintillation measurement or photometry after extraction with chloroform/methanol. The $IC_{50}$ values are determined from the inhibition curves (n=5, mean±SD).

Results: The relative order of the inhibitors, demonstrated in the $IC_{50}$ values, is indentical for both assays with lipid substrates (NAG and TAG). This fundamentally also applies to the water-soluble substrates, tributyrin, and PNPB, but some active compounds, which significantly reduce the HSL activity compared with NAG and TAG, are inactive in the inhibition of HSL compared with tributyrin and PNPB. This can be explained by an interference of these inhibitors with the lipid binding of the HSL (through the lipid binding domains), while the catalytic mechanism is not adversely affected. Water-soluble substrates are therefore cleaved from the HSL even in the presence of these inhibitors. The $IC_{50}$ values for inhibitors, which act even in the case of water-soluble substrates, generally lie between those for NAG and TAG as a substrate. This shows that NAG behaves as a "lipid-like" substrate for the HSL similarly to the authentic triglycerides and the NAG assay can be employed for finding inhibitors which block lipid binding (and the catalytic mechanism) of the HSL.

Example 6

Comparison of the Indirect NAG Assay with the Assays for TAG, PNPB, and Tributyrin

TABLE 6

| | $IC_{50}$, µM | | | |
|---|---|---|---|---|
| Compound | NAG assay | Tributyrin assay | PNPB assay | TAG assay |
| 1 | 0.85 ± 0.19 | 2.56 ± 0.45 | 3.56 ± 0.67 | 7.45 ± 1.36 |
| 2 | 1.06 ± 0.22 | 3.14 ± 0.38 | 5.03 ± 0.93 | 13.42 ± 2.44 |
| 3 | 2.14 ± 0.29 | >100 | >100 | 17.32 ± 1.96 |
| 4 | 3.18 ± 0.51 | >100 | 93.61 ± 7.92 | 20.45 ± 2.45 |
| 5 | 2.96 ± 0.47 | 4.09 ± 0.59 | 10.45 ± 0.66 | 25.34 ± 3.60 |
| 6 | 3.89 ± 0.38 | 65.54 ± 7.12 | >100 | 27.31 ± 4.05 |
| 7 | 4.56 ± 0.61 | 37.99 ± 6.35 | 75.34 ± 6.93 | 30.23 ± 3.66 |
| 8 | 4.94 ± 0.51 | 7.88 ± 1.12 | 12.55 ± 2.13 | 35.47 ± 4.05 |
| 9 | 7.24 ± 0.64 | 12.56 ± 3.05 | 19.87 ± 3.44 | 40.56 ± 3.55 |
| 10 | 8.55 ± 0.59 | 92.56 ± 8.45 | >100 | 52.38 ± 4.98 |
| 11 | 20.45 ± 3.05 | >100 | 90.45 ± 8.52 | 85.67 ± 7.34 |
| 12 | 26.78 ± 3.67 | 88.93 ± 7.75 | >100 | >100 |

Example 7

Influence of Various Detergents and Solvents on the Substrate Stability

NAG (0.05 mg/ml) is incubated at 37° C. for 180 min in the presence of increasing concentrations of various detergents and solvents and the extinction decrease at 550 nm (dissolution of the spec. substrate structure) is then determined (n=4, mean±SD).

Result: The substrate (phospholipid vesicles or micelles) exhibited different sensitivity compared with the agents employed. The extinction, (i.e., the amount of substrate) decreased in the presence of 1% DMSO by 10%, in the case of ethanol or methanol by at most 20%, in the case of 1% TX-100 or SDS by at most 30%. DMF was most efficient in dissolving the vesicles/micelles, and at 1% over 80% of NAG was released from the phospholipid/vesicle structures. The order in the efficiency of the solvents and detergents employed in the dissolution of the substrate structure is compatible with a shift in the extinction maximum (from 481 nm to 550 nm) by NAG, or of the chromophoric group (NBD) by incorporation into the apolar environment of phospholipid vesicles/micelles and the removal from aqueous environment caused thereby. Release of NAG from these structures in aqueous medium by dissolution of the vesicles/micelles (e.g., by detergents) or release of the chromophoric group as NBD fatty acid by lipolytic cleavage (by HSL) of NAG leads to a lowering of the extinction at 555 nm and an increase in the extinction at 481 nm. Vith the stability at 1% DMSO, the NAG substrate fulfils one of the basic requirements for a robust HTS assay.

Example 7

Influence of Various Detergents and Solvents on the Substrate Stability

TABLE 7

Absorption at 550 nm (arb. units)

| Conc. % | DMSO | DMF | TX-100 | SDS | Ethanol | Methanol |
|---|---|---|---|---|---|---|
| 0 | 3102 ± 288 | 3204 ± 259 | 3067 ± 284 | 3150 ± 321 | 3096 ± 241 | 3199 ± 280 |
| 0.05 | 3003 ± 259 | 3121 ± 294 | 3166 ± 308 | 3063 ± 288 | 3147 ± 288 | 3056 ± 243 |
| 0.1 | 3199 ± 302 | 2655 ± 308 | 3247 ± 253 | 2935 ± 254 | 3056 ± 213 | 3102 ± 276 |
| 0.2 | 2984 ± 273 | 1952 ± 299 | 3119 ± 277 | 2769 ± 275 | 3097 ± 253 | 2945 ± 241 |
| 0.5 | 3055 ± 289 | 1234 ± 234 | 2954 ± 248 | 2506 ± 301 | 2995 ± 231 | 2683 ± 210 |
| 1 | 2845 ± 254 | 654 ± 112 | 2154 ± 199 | 2296 ± 252 | 2834 ± 256 | 2534 ± 191 |
| 2 | 2317 ± 266 | 251 ± 82 | 956 ± 101 | 1413 ± 178 | 2510 ± 194 | 1985 ± 165 |
| 5 | 1432 ± 187 | 105 ± 42 | 489 ± 77 | 603 ± 89 | 1935 ± 163 | 1438 ± 121 |
| 10 | 372 ± 51 | 38 ± 10 | 167 ± 45 | 102 ± 12 | 873 ± 103 | 475 ± 92 |

Example 8

Influence of Various Detergents and Solvents on the Activity of the HSL

NAG (0.05 mg/ml) is incubated for 60 min with HSL (20 $\mu$g) in the presence of increasing concentrations of various agents. The extinction at 481 nm is determined (n=4, mean±SD).
Results: DMSO up to 1% reduced the amount of released NBD-FA by approximately 10%. As at this DMSO concentration up to 10% of NAG is released from the phospholipid vesicles/micelles by dissolution of the structures, a decrease in the enzyme activity by 20% results arithmetically. In the case of 0.5% DMSO, the reduction is still 10%. TX-100, acetone, ethanol, and methanol between 0.1 and 1% cause an increase in the HSL activity, possibly produced by a more efficient substrate presation. At high concentrations, they interfere with the activity. DMF leads to a significant loss in activity of the HSL, even at concentrations from 0.1%.

Example 8

Influence of Various Detergents and Solvents on the Activity of the HSL

Example 9

Cleavage of NAG by Lipases of Differing Specificity

NAG (0.05 mg/ml) is incubated for 60 min with 20 $\mu$g of partially purified HSL, 75 $\mu$g of partially purified LPL from rat adipocytes, 20 mU of bacterial lipase, 50 mU of pancreatic lipase, 100 mU of PLA$_2$ from snake venom, and 0.5 U of PC-specific phospholipase from Bacillus cereus. The increase in the extinction at 481 nm is determined (n=5, mean±SD).
Results: Under the optimized conditions given for HSL, the HSL (100%) and LPL (approximate 70%) exhibited the greatest activity. The bacterial and pancreatic lipase is markedly less active (25 or 1%), while the bacterial PC-specific phospholipase was virtually inactive. These strongly different activities show the specificity of the chosen conditions of the indirect NAG assay for the HSL, thus, for example, phospholipases possibly contained in coarse cell extracts are not detected. This data, however, also shows the applicability in principle of the assay principle to other lipases.

TABLE 8

Absorption at 481 nm (arb. units)

| Conc., % | DMSO | DMF | TX-100 | SDS | Ethanol | Methanol |
|---|---|---|---|---|---|---|
| 0 | 3534 ± 310 | 3427 ± 213 | 3451 ± 231 | 3325 ± 300 | 3510 ± 329 | 3523 ± 358 |
| 0.05 | 3423 ± 286 | 3365 ± 256 | 3642 ± 296 | 3948 ± 325 | 3776 ± 253 | 3421 ± 290 |
| 0.1 | 3320 ± 319 | 2576 ± 278 | 4164 ± 366 | 4487 ± 376 | 4093 ± 387 | 3341 ± 265 |
| 0.2 | 3301 ± 276 | 1321 ± 154 | 4976 ± 403 | 5876 ± 452 | 4894 ± 325 | 3150 ± 302 |
| 0.5 | 3199 ± 235 | 657 ± 102 | 4065 ± 312 | 6924 ± 537 | 4231 ± 296 | 2317 ± 194 |
| 1 | 3156 ± 196 | 210 ± 78 | 2156 ± 214 | 5421 ± 325 | 3541 ± 294 | 1948 ± 164 |
| 2 | 1488 ± 213 | 134 ± 55 | 1254 ± 143 | 2956 ± 132 | 2143 ± 215 | 1537 ± 78 |
| 5 | 945 ± 169 | 87 ± 32 | 548 ± 77 | 1523 ± 72 | 1327 ± 143 | 932 ± 93 |
| 10 | 272 ± 42 | 14 ± 5 | 315 ± 39 | 505 ± 49 | 423 ± 55 | 675 ± 70 |

Example 9

Cleavage of NAG by Lipases of Differing Specificity

TABLE 9

| | Increase in the absorption at 481 nm (arb. units) | | | | | |
|---|---|---|---|---|---|---|
| Enzyme, arb. units | HSL | LPL | Bacterial lipase | Pancreatic lipase | $PLA_2$ | PLC |
| 0 | 0 | 0 | 0 | 0 | 0 | 0 |
| 10 | 143 ± 18 | 105 ± 14 | 36 ± 7 | 9 ± 2 | 1 ± 1 | 0 |
| 20 | 321 ± 28 | 187 ± 17 | 81 ± 10 | 14 ± 4 | 3 ± 2 | 1 ± 1 |
| 50 | 744 ± 58 | 489 ± 31 | 148 ± 18 | 39 ± 7 | 5 ± 1 | 2 ± 2 |
| 75 | 1023 ± 95 | 773 ± 56 | 238 ± 29 | 64 ± 10 | 8 ± 2 | 2 ± 1 |
| 100 | 1287 ± 165 | 948 ± 72 | 341 ± 39 | 92 ± 14 | 10 ± 2 | 3 ± 1 |
| 150 | 2106 ± 183 | 1487 ± 132 | 467 ± 57 | 140 ± 18 | 26 ± 6 | 3 ± 1 |
| 200 | 2697 ± 231 | 1952 ± 173 | 748 ± 70 | 188 ± 21 | 35 ± 9 | 5 ± 2 |
| 250 | 3321 ± 349 | 2638 ± 213 | 904 ± 83 | 234 ± 30 | 46 ± 12 | 5 ± 2 |
| 300 | 3855 ± 288 | 2945 ± 250 | 1056 ± 143 | 265 ± 34 | 54 ± 9 | 7 ± 3 |
| 400 | 4427 ± 402 | 3512 ± 288 | 1270 ± 187 | 286 ± 32 | 75 ± 11 | 10 ± 3 |

Example 10

Cleavage of Compound (3) Modified with NBD Fatty Acid by HSL

Compound (3) (0.05mg/ml) is incubated with 20 µg of partially purified HSL. The extinction at 481 nm is determined at specific times (n=5, mean±SD).
Results: See Example 10, Table 10.

Example 10

Cleavage of Compound (3) Modified with NBD Fatty Acid by HSL

TABLE 10

| Increase in the absorption at 481 nm (arb. units) | |
|---|---|
| Time, min | Compound 3 |
| 0 | 0 |
| 1 | 39 ± 5 |
| 2 | 67 ± 9 |
| 5 | 158 ± 19 |
| 10 | 378 ± 41 |
| 15 | 561 ± 51 |
| 20 | 789 ± 93 |
| 30 | 1210 ± 193 |
| 45 | 1784 ± 204 |
| 60 | 2386 ± 234 |
| 75 | 2873 ± 259 |
| 90 | 3607 ± 402 |
| 120 | 4312 ± 389 |
| 180 | 4905 ± 423 |

Example 11

Inhibition of the HSL by Diisopropyl Phosphofluoridate

NAG (0.05 mg/ml) is incubated for 60 min with 20 µg of partially purified HSL in the presence of increasing concentrations of diisopropyl phosphofluoridate. The increase in the extinction at 481 nm is determined in aliquots of the reaction batches (indirect NAG assay), or after extraction with chloroform/methanol the amount of released NBD-FA in the organic phase is determined by fluorimetry (direct NAG assay). Alternatively, incubations of the HSL with TAG as substrate (see above) are carried out and the amount of radiolabeled oleic acid released is determined after extraction with chloroform/methanol. The cleavage activity in the absence of inhibitor is set at 100% for each assay (n=7, mean±SD).

Result: In all three assays, typically sigmoidal inhibition curves resulted for diisopropyl phosphofluoridate. The $IC_{50}$ values calculated therefrom did not differ significantly from one another for the indirect (0.8 mM) or direct NAG assay (1.1 mM). A somewhat higher $IC_{50}$ value of 2.1 mM is calculated for the cleavage of trioleoylglyceride. This is in accord with the differences found above in the inhibitory actions of various inhibitors, which are observed with these assays (see Example 6 for possible explanations). Independently of this, the $IC_{50}$ values determined for the inhibition of HSL by diisopropyl phosphofluoridate by the indirect NAG assay are very much in accord with published data (P. Stralfors, H. Olsson, P. Belfrage, *The Enzymes* XVIII (1987) 147–177; P. Stralfors, P. Belfrage, *J. Biol. Chem.* 258 (1983) 15146–15151; P. Belfrage, B. Jergil, P. Stralfors, H. Tornquist, *FEBS Lett.* 75 (1977) 259–263).

Example 11

Inhibition of the HSL by Diisopropyl Phosphofluoridate

TABLE 11

| | % of maximal HSL Activity | | |
|---|---|---|---|
| Conc., mM | NAG assay | NBD-FA released | TAG Assay |
| 0 | 100 | 100 | 100 |
| 0.01 | 98.9 ± 5.3 | 99.6 ± 4.6 | 99.4 ± 6.2 |
| 0.02 | 96.2 ± 5.1 | 97.4 ± 5.0 | 98.8 ± 5.9 |
| 0.05 | 92.1 ± 4.1 | 94.3 ± 4.4 | 97.5 ± 5.1 |
| 0.1 | 84.3 ± 5.1 | 88.4 ± 5.1 | 95.1 ± 4.5 |
| 0.2 | 74.5 ± 6.3 | 79.2 ± 4.9 | 89.5 ± 5.3 |
| 0.5 | 61.5 ± 5.7 | 67.4 ± 5.3 | 78.9 ± 6.4 |
| 1 | 44.6 ± 4.4 | 53.8 ± 4.9 | 66.3 ± 5.7 |
| 2 | 27.8 ± 3.1 | 38.6 ± 3.4 | 51.9 ± 4.4 |
| 5 | 16.5 ± 2.5 | 24.7 ± 2.8 | 36.7 ± 4.9 |
| 10 | 10.6 ± 1.7 | 13.6 ± 1.9 | 22.6 ± 3.5 |
| 20 | 5.7 ± 1.3 | 7.7 ± 1.5 | 11.8 ± 1.9 |
| 50 | 3.5 ± 1.1 | 4.5 ± 1.2 | 6.4 ± 1.3 |
| 100 | 2.5 ± 0.8 | 2.7 ± 0.6 | 3.1 ± 0.4 |

Example 12

Feasibility of the Indirect NAG Assay in the Microtiter Plate Format

NAG (0.05 mg/ml) is incubated for different times with partially purified HSL in an assay volume of 200 μl in wells of 96-hole microtiter plates. The extinction at 481 nm is determined in a microtiter plate reader.
Result: Under the conditions chosen, the reaction is linear down to approximately 60 min. The variance (SD) is in this case between 4 and 7%. The indirect NAG assay is thus suitable for use in HTS.

Example 12

Feasibility of the Indirect NAG Assay in the Microtiter Plate Format

TABLE 12

Increase in the absorption at 481 nm (arb. units)

| Time, min | Test: 1 | Test: 2 | Test: 3 | Test: 4 | Test: 5 | Test: 6 | Test: 7 | Test: 8 |
|---|---|---|---|---|---|---|---|---|
| 0 | 0 | 0 | 0 | 0 | 0 | 0 | 0 | 0 |
| 1 | 50 | 48 | 61 | 49 | 56 | 52 | 57 | 49 |
| 2 | 97 | 89 | 107 | 95 | 101 | 116 | 93 | 89 |
| 5 | 238 | 269 | 278 | 243 | 277 | 248 | 235 | 241 |
| 10 | 487 | 534 | 462 | 458 | 552 | 508 | 488 | 460 |
| 15 | 713 | 768 | 709 | 712 | 789 | 780 | 735 | 718 |
| 20 | 978 | 1013 | 967 | 979 | 1097 | 1121 | 1045 | 966 |
| 30 | 1413 | 1579 | 1625 | 1690 | 1523 | 1688 | 1452 | 1410 |
| 45 | 2045 | 2134 | 2239 | 2106 | 2106 | 2238 | 1967 | 2145 |
| 60 | 2367 | 2541 | 2658 | 2755 | 2534 | 2608 | 2536 | 2690 |
| 75 | 2611 | 2894 | 2973 | 3023 | 2871 | 2879 | 2982 | 2895 |
| 90 | 2985 | 3244 | 3310 | 3355 | 3260 | 3122 | 3240 | 3125 |
| 120 | 3127 | 3469 | 3577 | 3601 | 3489 | 3378 | 3507 | 3320 |

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

| Abbreviations used: | |
|---|---|
| arb. units | Arbitrary units |
| BSA | Bovine serum albumin |
| cAMP | Cyclic adenosine monophosphate |
| DCC | Dicyclohexylcarbodiimide |
| DMF | N,N-Dimethylformamide |
| DMSO | Dimethyl sulfoxide |
| DTT | Dithiothreitol |
| EDTA | Ethylenediamine-N,N,N',N'-tetraacetic acid |
| FAB-MS | Fast atom bombardment mass spectrometry |
| HSL | Hormone-sensitive lipase |
| HTS | High-throughput screening |
| $Kp_i$ | Potassium dihydrogenphosphate/potassium phosphate buffer |
| LPL | Lipoprotein lipase |
| NAG | NBD-monoacylglyceride: 2,3-dihydroxypropyl 12-(7-nitro benzo[1,2,3]oxadiazol-4-ylamino)dodecanoate |
| NBD | 4-Chloro-7-nitrobenzo-2-oxa-1,3-diazole |
| NBD-FA | NBD fatty acid: 12-(7-nitrobenzo[1,2,3]oxadiazol-4-ylamino)-dodecanoic acid |
| NIDDM | Non insulin-dependent diabetes mellitus |
| PC | Phosphatidylcholine |
| PI | Phosphatidylinositol |

| -continued | |
|---|---|
| Abbreviations used: | |
| $PLA_2$ | Phospholipase $A_2$ |
| PLC | Phospholipase C |
| PNPB | p-Nitrophenyl butyrate |
| SD | Standard deviation |
| SDS | Sodium dodecyl sulfate |
| TAG | [$^3$H]-Trioleoylglycerol |
| TRIS | Tris(hydroxymethyl)aminomethane |
| TLC | Thin-layer chromatography |
| TX-100 | Triton ® X-100 |

What is claimed is:

1. A process for preparing a micelle or vesicle substrate comprising a monoacylglyceride having a fluorescent label comprising a monoacylglyceride having a fluorescent label, comprising:
    (a) reacting a fatty acid having a fluorescent label with 2,3-epoxypropanol to give a monoacylglyceride in an alcoholic solution at room temperature with addition of a base; and
    (b) subjecting the monoacylglyceride to an ultrasonic treatment with phospholipids in a ratio from approximately 1:10 to 10:1 mg/ml, to produce the substrate, wherein the substrate chances color from yellow to red with formation of micelles or vesicles.

2. A process for determining whether a test substance contains lipases comprising:
    (a) preparing a micelle or vesicle substrate comprising a monoacylglyceride having a fluorescent label by:
        (1) reacting a fatty acid having a fluorescent label with 2,3-epoxypropanol to give a monoacylglyceride in an alcoholic solution at room temperature with addition of a base; and
        (2) subjecting the monoacylglyceride to an ultrasonic treatment with phospholipids in a ratio from approximately 1:10 to 10:1 mg/ml to produce the substrate, wherein the substrate changes color from yellow to red with formation of micelles or vesicles;
    (b) incubating a test substance with the micelle or vesicle substrate
    (c) determining a color change from red to yellow, wherein the color change indicates the presence of a lipase.

3. The process of claim 2, wherein the determining is accomplished with high-throughput screening.

4. A process for determining activity of a lipase, comprising:
    (a) preparing a micelle or vesicle substrate comprising a monoacylglyceride having a fluorescent label by:
        (1) reacting a fatty acid having a fluorescent label with 2,3-epoxypropanol to give a monoacylglyceride in an alcoholic solution at room temperature with addition of a base; and
        (2) subjecting the monoacylglyceride to an ultrasonic treatment with phospholipids in a ratio from approximately 1:10 to 10:1 mg/ml to produce the substrate, wherein the substrate changes color from yellow to red with formation of micelles or vesicles;
    (b) incubating the lipase with the micelle or vesicle substrate; and
    (c) determining a rate of color change from red to yellow, wherein the rate of color change correlates with lipase activity.

5. The process of claim 4, wherein the lipase is a hormone-sensitive lipase.

6. A process for determining whether a test substance contains lipase inhibitors comprising:

(a) preparing a micelle or vesicle substrate comprising a monoacylglyceride having a fluorescent label by:
   (1) reacting a fatty acid having a fluorescent label with 2,3-epoxypropanol to give a monoacylglyceride in an alcoholic solution at room temperature with addition of a base; and
   (2) subjecting the monoacylglyceride to an ultrasonic treatment with phospholipids in a ratio from approximately 1:10 to 10:1 mg/ml to produce the substrate, wherein the substrate changes color from yellow to red with formation of micelles or vesicles;

(b) in a pre-incubation mixture, pre-incubating a test substance with the micelle or vesicle substrate (c) adding a lipase to the pre-incubation mixture of step (b); and (d) determining a color change from red to yellow, wherein a lack of color change indicates lipase inhibitor activity.

7. The process of claim 6, wherein the determining is accomplished with high-throughput screening.

8. A process for determining activity of a lipase inhibitor comprising:

(a) preparing a micelle or vesicle substrate comprising a monoacylglyceride having a fluorescent label by:
   (1) reacting a fatty acid having a fluorescent label with 2.3-epoxypropanol to give a monoacylglyceride in an alcoholic solution at room temperature with addition of a base; and
   (2) subjecting the monoacylglyceride to an ultrasonic treatment with phospholipids in a ratio from approximately 1:10 to 10:1 mg/ml to produce the substrate, wherein the substrate changes color from yellow to red with formation of micelles or vesicles;

(b) in a pre-incubation mixture, pre-incubating a lipase inhibitor with the micelle or vesicle substrate;

(c) adding a lipase to the pre-incubation mixture of step (b);

(d) determining a rate of color change from red to yellow, wherein the rate of color change correlates with lipase inhibitor activity.

9. The process of claim 8, wherein the lipase is a hormone-sensitive lipase.

* * * * *